United States Patent [19]

Trudell et al.

[11] Patent Number: 5,244,930
[45] Date of Patent: Sep. 14, 1993

[54] BIPHASIC FOAM BLOOD MASS TRANSFER DEVICE

[75] Inventors: Leonard A. Trudell, Warwick, R.I.; Anthony D. Whittemore, Sherborn, Mass.

[73] Assignee: Brigham and Women's Hospital, Boston, Mass.

[21] Appl. No.: 806,307

[22] Filed: Dec. 13, 1991

[51] Int. Cl.$^5$ .................... C08J 9/00; A61M 1/14; A61M 1/34

[52] U.S. Cl. .................... 521/99; 521/155; 521/905; 422/45; 422/46; 422/47; 422/48; 428/304.4; 210/496

[58] Field of Search .................... 422/45–48; 261/DIG. 28; 128/DIG. 3; 55/16, 158, 178; 210/496, 510.1; 521/99, 155, 905; 428/304.4

[56] References Cited

U.S. PATENT DOCUMENTS

| | | | |
|---|---|---|---|
| 3,070,092 | 12/1962 | Wild et al. | 128/214 |
| 3,204,631 | 9/1965 | Fields | 128/214 |
| 3,212,498 | 10/1965 | McKirdy et al. | 128/214 |
| 3,733,776 | 5/1973 | Li et al. | 55/16 |
| 3,915,650 | 10/1975 | Talonn et al. | 261/DIG. 28 |
| 3,998,593 | 12/1976 | Yoshida et al. | 55/158 |
| 4,058,369 | 11/1977 | Bentley et al. | 128/DIG. 3 |
| 4,073,622 | 2/1978 | Luppi | 128/DIG. 3 |
| 4,158,693 | 6/1979 | Reed et al. | 422/46 |
| 4,182,739 | 1/1980 | Curtis | 422/47 |
| 4,228,125 | 10/1980 | Lobdell et al. | 422/46 |
| 4,261,951 | 4/1981 | Milev | 422/46 |
| 4,280,981 | 7/1981 | Harnsberger | 422/46 |
| 4,328,102 | 5/1982 | Bellhouse et al. | 261/DIG. 28 |
| 4,336,224 | 6/1982 | Siposs | 422/46 |
| 4,374,088 | 2/1983 | Stenberg et al. | 422/46 |
| 4,428,934 | 1/1984 | Raible | 424/101 |
| 4,666,668 | 5/1987 | Lidorenko et al. | 422/48 |
| 4,698,207 | 10/1987 | Bringham et al. | 422/46 |
| 4,874,581 | 10/1989 | Sutherland et al. | 422/46 |

OTHER PUBLICATIONS

W. R. Grace & Co. HYPOL ™ Product Literature.

Primary Examiner—James C. Housel
Assistant Examiner—N. Bhat
Attorney, Agent, or Firm—Sterne, Kessler, Goldstein & Fox

[57] ABSTRACT

The present invention relates to apparatus for transferring constituents into and out of a fluid such as blood. The apparatus includes a biphasic foam body which functions as a blood oxygenator, blood dialyzer, or other blood mass transfer device.

20 Claims, 2 Drawing Sheets

BIPHASIC FOAM BLOOD MASS TRANSFER DEVICE

FIELD OF THE INVENTION

The present invention relates to apparatus for transferring constituents into and out of blood. More particularly, the invention uses a biphasic foam as a blood oxygenator or dialyzer.

BACKGROUND OF THE INVENTION

The field of this invention is blood mass transfer devices, particularly oxygenators, wherein some desirable constituent (e.g., oxygen) is transferred into the blood and/or some undesirable constituent (e.g., carbon dioxide) is transferred out of the blood. Three basic types of oxygenators have developed over time: film oxygenators (e.g., U.S. Pat. No. 3,070,092), bubble oxygenators (e.g., U.S. Pat. Nos. 3,915,650 and 4,428,934); and membrane oxygenators (e.g., U.S. Pat. No. 4,698,207).

Film oxygenators are characterized by exposing a continuous thin film of blood to an oxygen atmosphere. The surface upon which the blood is filmed must be chemically inert and not damage the blood. Additionally, the surface must sustain a very thin film in order to maximize the diffusion of oxygen into the blood. In bubble oxygenators, oxygen is introduced into the blood as bubbles which oxygenate the blood and drive off carbon dioxide. In these oxygenators, the bubbling or foaming mixture must be passed through a "defoamer" to eliminate gas bubbles from the oxygenated blood before it is returned to the patient. In a typical membrane oxygenator, blood is carried in or around hollow membrane fibers. Oxygen passes through the membrane from an oxygen-rich gas stream to the bloodstream, and carbon dioxide passes through the membrane from the blood to the gas stream. The number and size of the hollow membrane fibers are selected to transfer sufficient oxygen to satisfy the metabolic requirements of the patient. Before the blood is returned to the patient from the membrane oxygenator, it is usually passed through a filter to remove any particulate emboli or gas bubbles. The filter is usually in the arterial line outside of the oxygenator itself.

Various types and configurations of foam have been used for specific purposes in bubble and film oxygenators. Blood oxygenators which use foam material to "defoam" the blood-oxygen mixture, i.e., remove bubbles from the blood, are well known as illustrated by the blood oxygenator in U.S. Pat. No. 4,158,693 to Reed et al. Foam material is also used in the Reed et al. bubble oxygenator to provide an enlarged surface area for oxygen-blood contact, and to disperse the blood so it will rise uniformly through the oxygenating chamber. The film oxygenator in U.S. Pat. No. 3,070,092 to Wild et al. uses a porous sponge material as the surface on which the blood is filmed. None of these types of oxygenators contemplates using a foam material as both the blood pathway and the membrane across which oxygenation occurs.

Certain parameters must be considered when designing an oxygenator, whether of the film, bubble, or membrane type. Parameters which must be considered include the overall size and geometry of the oxygenator, blood volume that can be oxygenated, damage to the blood, the rate of gas exchange, and the volume of blood physically held by the oxygenator (known as "priming volume").

The physical size of an oxygenator is determined in large part by the effective exchange surface area, that is, the exchange surface area the blood is exposed to for oxygenation. The total volume of blood that can be oxygenated must be sufficient to satisfy the metabolic requirements of a patient. As discussed in U.S. Pat. No. 4,698,207 to Bringham et al., this can require using 41,000 to 71,000 hollow fibers in a hollow fiber membrane oxygenator. In order to minimize the size of a blood oxygenator, a large exchange surface area must be contained in a small volume. As a result, the exchange surface area may have to assume intricate geometries which is made difficult by the structures of conventional membrane oxygenators. Intricate geometries are also difficult to achieve with conventional film and bubble oxygenators, as illustrated by the grid of plates in the film oxygenator in U.S. Pat. No. 3,070,092 to Wild et al. and the aluminum oxygenator tubes in U.S. Pat. No. 4,280,981 to Harnsberger.

Blood is a very delicate body tissue and is damaged when handled and exposed to foreign surfaces and gas atmospheres. Requiring the blood to flow through or around fibers or through tubes composed of substances such as aluminum or styrenes physically damage the blood by denaturation of proteins and mechanical damage to cells and formed elements.

In film and bubble oxygenators, the oxygen diffuses directly into the blood from the oxygen-rich atmosphere; carbon dioxide diffuses out of the blood to that atmosphere. In the membrane oxygenator, the oxygen and carbon dioxide diffusion take place across a permeable membrane. The design of the oxygenator, e.g., choice of membrane material, should maximize the rate of gas exchange, that is, the rate of absorption of the oxygen by the blood without exposing the blood directly to a gas atmosphere.

It is apparent that a blood oxygenator which maximizes the rate of gas exchange may require a large exchange surface area and oxygenator volume, and may also damage the blood. The design parameters conflict such that optimizing one parameter may degrade another. Therefore, the problem remains to optimize all the parameters to design a blood oxygenator that has a large exchange surface area per unit volume, can take on different geometries, minimizes damage to the blood, and maximizes the rate of gas exchange.

The same conflicting parameters exist for other mass transfer devices, such as dialyzers. Dialyzers perform the function of removing metabolic waste products without removal of essential constituents such as proteins. The problem to be solved here, analogous to that of blood oxygenators, is to design a dialyzer which has a large exchange surface area per unit volume, can take on different geometries, minimizes damage to the blood, and maximizes the rate of removal of the waste products from the blood.

Accordingly, prior to the development of the present invention, no single blood mass transfer device provided a large exchange surface area in a small volume capable of different geometries, and which minimized damage to the blood while providing a high rate of mass transfer. It is therefore an object of the present invention to provide a mass transfer device which has a large exchange surface area in a small volume, and which minimizes damage to the blood while achieving a high rate of mass transfer. It is a further object of this invention to provide a blood oxygenator which has a large exchange surface area in a small volume, and which minimizes damage to the blood while achieving a high rate of gas exchange. It is a further object of this invention to provide a blood dialyzer which has a large exchange surface area in a small volume, and which minimizes damage to the blood while achieving a high rate of molecular transport. It is a feature of this invention to use a pliable foam material in the mass transfer device as both the blood pathway and the membrane across which the transfer occurs. It is an additional feature of this invention that the blood mass transfer devices can take on varied and intricate geometries to satisfy the requirements of the particular application.

SUMMARY OF THE INVENTION

The present invention is a device for facilitating the exchange of constituents into and out of a fluid such as blood. The device includes a body of a pliable open-cell foam material. The open-cell structure forms channels through which the blood flows. These channels are formed of inter-connecting cells within the foam body lined by a skin (or membrane) which forms as a consequence of the manner in which the material itself polymerizes. The paths of these channels through the foam body are random and very varied or "tortuous." When blood is the fluid flowing through the channels, a polyurethane foam is preferable due to its excellent blood handling properties.

The rest of the cells in the foam body are open and not sealed by the foam membrane; these cells constitute the matrix of the material. In one aspect of the invention, these cells form a gas pathway to allow oxygen to migrate throughout the foam material and across the membrane into the blood while allowing carbon dioxide to migrate across the membrane out of the blood. Porous fibers can be used in the gas pathway portion of the foam body to more efficiently distribute oxygen throughout the foam body. The porous fibers are contained within the foam matrix and do not come in contact with blood.

When configured as a blood oxygenator, a hydrophilic ("wettable") foam can be used so that water from the plasma portion of blood wets the membrane. Oxygen and carbon dioxide are both carried in aqueous solution, dissolved in the water portion of plasma, and are therefore easily transferred across the membrane.

In another aspect, the unsealed cells form a dialysate pathway for transport of molecules out of the blood. The blood flows through the skinned channels and the molecules migrate across the skin membrane from the blood into the dialysate.

In a third aspect of the invention, the fluid flowing through the skinned channels can be a fluid other than blood. The unsealed portion of the foam body can then contain a gas, or another fluid, so that the gas or fluid constituents will migrate across the membrane into or out of the fluid in the skinned channels.

BRIEF DESCRIPTION OF THE DRAWINGS

Various objects, features, and advantages of the present invention will be more fully appreciated as the same becomes better understood from the following detailed description of the present invention when considered in connection with the accompanying drawings, in which.

DETAILED DESCRIPTION OF THE DRAWINGS

Figure 1:
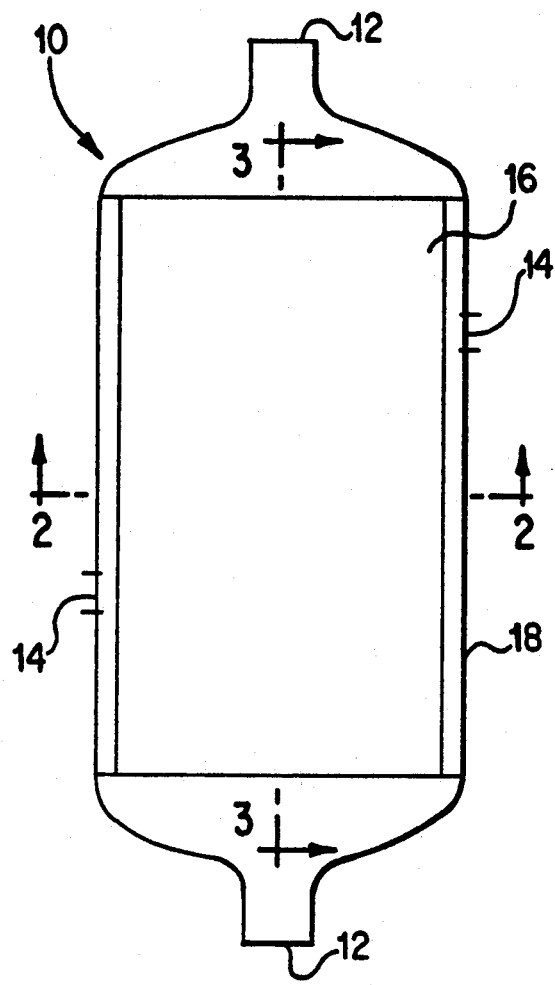
FIG. 1 shows a blood oxygenator comprising the foam material configured as a cylinder.

With continuing reference to the drawing figures in which similar reference numerals are used throughout the description to describe similar features of the invention, FIG. 1 shows a blood oxygenator 10 configured with a foam cylinder 16 potted within a housing 18. The blood can enter through either access port 12 and flow through the oxygenator while the oxygen can enter/exit through either access port 14, as the design is symmetrical.

The blood oxygenator 10 in FIG. 1 receives oxygen-poor (venous) blood from the patient into access port 12 through devices and tubing which are well known in the blood oxygenator art. Similarly, once the blood has been oxygenated, the oxygen-rich blood is returned to the patient via well known devices. The oxygen source which is connected to the blood oxygenator 10 at access port 14 is also one commonly used in blood oxygenation.

Figure 2:
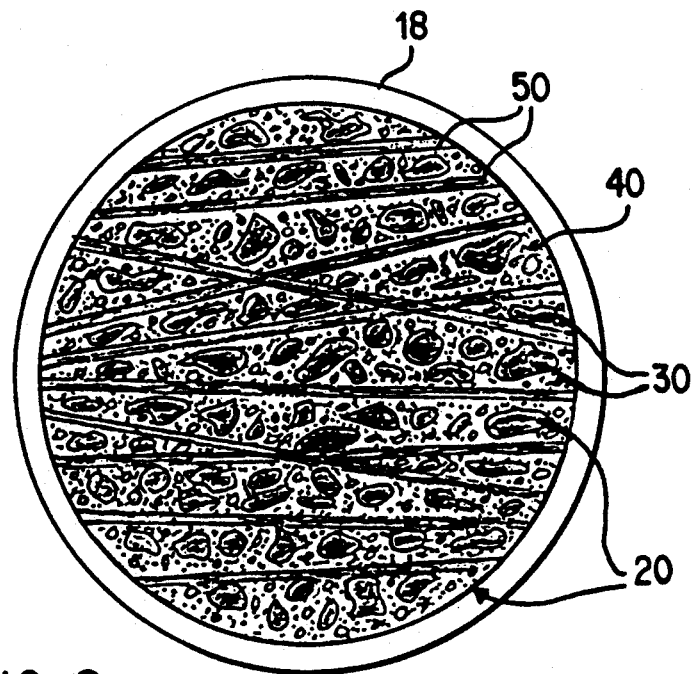
FIG. 2 shows a cross section of a foam cylinder taken along line 2—2 in FIG. 1.

FIG. 2 shows a cross section of the foam cylinder 16 from FIG. 1. The foam cylinder comprises two series of voids which constitute two distinct phases or portions of the foam. The first portion comprises the large voids which form the blood channels or blood pathway 30. The large voids are interconnected and "skinned" with the foam material to form a skinned layer or membrane 20 on the voids, thus forming channels. These channels take on random, tortuous paths and define blood channels or blood pathway 30. Due to the random, tortuous paths of the blood channels 30, the blood pathway confines a large surface area in a small volume.

Figure 3:
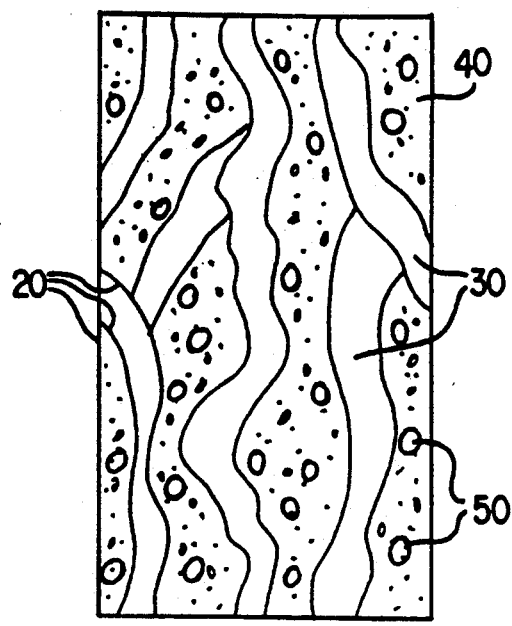
FIG. 3 shows an enlarged cross section of a foam cylinder taken along line 3—3 in FIG. 1.

The second portion of the foam cylinder 16 comprises the smaller voids of cells in the foam body which are not "skinned"; these cells constitute the matrix of the material. Some cells in this portion may be interconnected, but all the cells in this portion are unsealed and form the gas pathway 40 for the delivery of oxygen to and removal of carbon dioxide from the blood. To minimize gas diffusion distances, hollow porous fibers 50 carry the gases throughout the foam cylinder to cut down the diffusion distance between the source of the gas and the blood pathway 30. The porous fibers 50 are shown in FIG. 2 and FIG. 3 as perpendicular to the blood pathway 30. However, the porous fibers are not restricted to such a configuration and could be parallel or at any angle to the blood pathway.

FIG. 3 shows a vertical cross section of the foam cylinder 16 which illustrates the random and tortuous nature of the blood pathway 30. The porous fibers 50 serve to distribute the gas within the foam cylinder to minimize the diffusion distance. The porous fibers are contained within the foam matrix and do not come in contact with blood. Without the porous fibers, oxygen would have to diffuse from the source on one side of the foam cylinder, shown at 14 in FIG. 1, all the way through to the other side. The porous fibers act as a ventilation system to deliver the oxygen and remove the carbon dioxide throughout the foam cylinder more efficiently.

Figure 4:
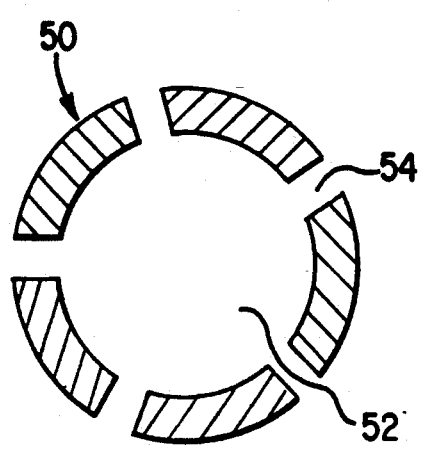
FIG. 4 shows a highly enlarged cross section of a porous fiber which distributes oxygen throughout the foam cylinder.

As shown in FIG. 4, the fibers 50 are porous, thus allowing molecules to pass into and out of the gas channel 52 through the pores 54. In the preferred embodiment, the fiber is hydrophobic ("non-wettable") so no fluids pass into the fiber channel, with pore size sufficient to allow molecules of oxygen and carbon dioxide to easily exit and enter the porous fibers. For example, porous fibers made of polyacrylonitrile can be used, such as the DIAFLO TM ultra-filter XM50 sold by Amicon, which has a pore size of 50,000 amu (atomic mass units).

Figure 5:
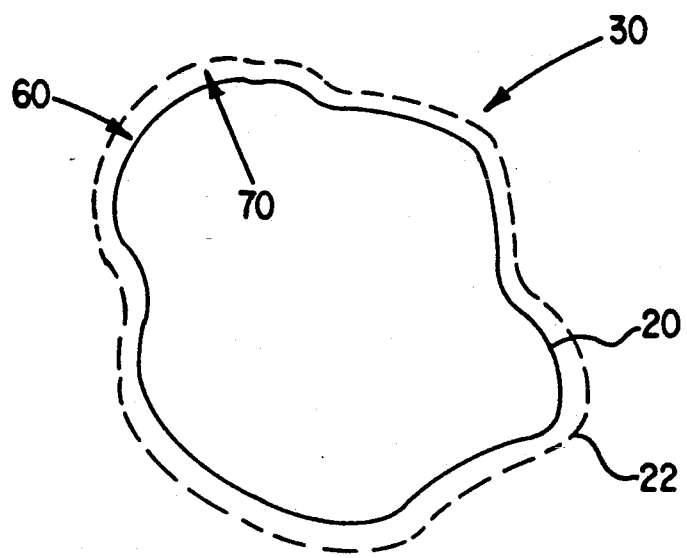
FIG. 5 shows a cross section of a blood channel illustrating the diffusion across the skin membrane.

FIG. 5 illustrates the process by which oxygenation takes place within the foam cylinder. A blood channel 30, defined by the skinned membrane 20, is shown in FIG. 5. As the skinned membrane is hydrophilic, water from the blood wets the skinned membrane to form a layer wetted with water 22. As oxygen is soluble in water, the oxygen from the surrounding gas pathway or gas phase of the foam cylinder dissolves in the water of the wetted membrane 22 as shown by the arrow 60. Similarly, carbon dioxide is also soluble in water, and the carbon dioxide in the blood channel 30 also dissolves in the water of the wetted membrane 22 as shown by the arrow 70. In this manner, water becomes the functional membrane and serves as the gas transport medium. Once dissolved in the water, oxygen will then migrate into the blood and carbon dioxide will migrate into the surrounding gas phase as a result of the diffusion gradient since both gases will be moving from an area of high concentration to an area of low concentration. More particularly, carbon dioxide is in high concentration in the blood and oxygen is in high concentration in the gas phase of the foam cylinder. Therefore, a diffusion gradient is established such that oxygen will migrate from the gas phase into the blood in the blood channel, and carbon dioxide will migrate from the blood in the blood channel to the gas phase of the foam cylinder. The wetted membrane 22 allows this transfer to take place across the membrane due to the solubility of the two gases in water.

In the preferred embodiment, the foam cylinder, or other foam body, is comprised of a hydrophilic, polyurethane open cell foam such as HYPOL TM 5100. HYPOL TM foams are commercially available from W. R. Grace & Co. HYPOL TM foams have excellent blood handling properties. They are biocompatible in that there is little chemical reaction with the blood or tissues, or extraction into the blood of foreign material such as plasticizers. HYPOL TM 5100, configured as a foam cylinder as shown in FIG. 1, can be used with pressures comparable to human blood pressure, and above human blood pressure, as may be found in heart-lung machine circuits.

HYPOL TM polymers are a family of foamable hydrophilic polyurethane prepolymers derived from toluene diisocyanate or methylene diphenylisocyanate (MDI). HYPOL TM 5100 is one of the HYPOL TM Plus MDI-based prepolymers. In the production of polyurethane foams, excess isocyanate groups in the polymer react with water to produce carbon dioxide which "blows" the foam at the same time that crosslinking is occurring. This results in a crosslinked product containing bubbles of trapped carbon dioxide. The "skin" forms as a consequence of phase interface phenomena because the gases that "blow", or form, the foam structure are generated by chemical reaction between the pre-polymer and solvent (water) within the material itself.

The porous fibers used to carry the gases in the blood oxygenator embodiment are placed in with the reactants prior to adding the water or carboxylic acids so that the reaction occurs around the porous fibers. In this way, the foam forms around the fibers, so that the fibers are included in the matrix of the foam. Additionally, surfactants such as silicone or Pluronic L-62 and P-75 (BASF Wyandotte Corporation) are added so that the bubbles formed during the "blowing" process result in a three dimensional array of sealed, connected voids. The sealed, connected voids form random channels, each of which takes a tortuous path. As a result, the foam body comprises a multiplicity of channels containing a large surface area in a small volume. Although the Figures show a foam cylinder, the foam can be produced in varied and intricate geometries and still comprise a multiplicity of channels containing a large surface area in a small volume.

When configured as a blood oxygenator, the blood travels in the skinned channels and the second portion of the foam body contains the gas pathway, with diffusion of oxygen and carbon dioxide occurring across the skin membrane. The foam body can also be configured to perform dialysis by making a minor modification to the polymer molecular weight of the HYPOL TM foam. The foam with the modified molecular weight retains its blood handling properties and the blood still flows through the skinned channels. However, the second portion of the foam body, the matrix, becomes a dialysate pathway rather than a gas pathway.

Dialysate is a solution of electrolytes and other naturally occurring solutes at concentrations normally found in the blood at physiologic concentration. The molecules of metabolic waste products (e.g., excess sodium or excess potassium, urea, creatinine, etc.) will migrate across the skinned membrane from the blood to the dialysate phase because of the concentration gradient established. That is, the concentration in the blood of sodium, potassium, and metabolic waste products is higher than the concentration in the dialysate phase of the foam body. Waste products from the blood (e.g., creatinine, urea, etc.) will migrate across the membrane from the blood in the blood channel into the dialysate phase of the foam body because of the concentration gradient. That is, the concentration of waste products in the blood is higher than the concentration of the waste products in the dialysate phase of the foam body. The molecular weight and resulting porosity of the foam are selected to allow transport across the membrane of low and middle molecular weight molecules, but not protein molecules, which are large, complex molecules, and which must be retained within the blood.

The invention which is intended to be protected herein should not be construed as limited to the particular forms disclosed, as these are to be regarded as illustrative rather than restrictive. For example, the foam body could be used as any blood mass transfer device, and is not limited to use as an oxygenator or dialyzer, and the geometries of the foam body are not limited to a cylinder. Additionally, the foam body could be used as a mass transfer device between a fluid other than blood, and another fluid or a gas.

Variations and changes may be made by those skilled in the art without departing from the spirit of the invention. Accordingly, the foregoing detailed description should be considered exemplary in nature are not limited to the scope and spirit of the invention as set forth in the following claims.

What is claimed is:

1. A biphasic foam structure comprising:
 a first open-celled phase formed of cells disposed within said foam structure;
 a second phase formed by a permeable membrane which creates interconnected cells to define a channel within said foam structure.

2. A foam structure according to claim 1 wherein said foam structure comprises polyurethane.

3. A foam structure according to claim 1 further comprising a plurality of porous fibers disposed within said first phase.

4. A blood oxygenator comprising:
 a body of hydrophilic, open-cell biphasic foam;
 blood connection means connected to said body for transporting blood into and out of said body;
 a first phase of said body comprising cells, said cells forming a gas pathway;
 a second phase of said body formed by a gas permeable membrane comprised of said foam which creates interconnected cells to define a channel within said body, said channel forming a blood pathway, wherein said gas permeable membrane separates said channel from said first phase so that water from blood in said blood pathway wets said membrane such that oxygen within said gas pathway dissolves in the water and carbon dioxide from the blood in said blood pathway dissolves in the water, whereby oxygen is transferred across said membrane into the blood and carbon dioxide is transferred across said membrane out of the blood.

5. A blood oxygenator according to claim 4, wherein said first phase of said body is comprised of cells not sealed by said membrane.

6. A blood oxygenator according to claim 5, wherein said first phase of said body further comprises a plurality of porous fibers disposed within said body for distributing oxygen within said body.

7. A blood oxygenator according to claim 4, wherein said second phase of said body further comprises a plurality of said channels randomly disposed within said body, wherein each said channel follows a tortuous path.

8. A blood oxygenator according to claim 7, wherein said first phase of said body further comprises a plurality of porous fibers disposed within said body for distributing oxygen within said body.

9. A blood mass transfer device comprising:
 a body of biphasic, open cell foam;
 blood connection means connected to said body for transporting blood into and out of said body;
 a first phase of said body formed of cells within said body defining a first pathway through said body for gas;
 a second phase of said body formed by a permeable membrane comprised of said foam which creates interconnected cells to define a channel within said body, said permeable membrane separating said channel from said first phase so that said channel forms a second pathway for blood.

10. A blood mass transfer device according to claim 9, wherein said cells of said first phase are not sealed by said membrane.

11. A blood mass transfer device according to claim 9, wherein said body of biphasic, open cell foam comprises hydrophilic foam.

12. A blood mass transfer device according to claim 9, wherein said channel follows a tortuous path.

13. A blood mass transfer device according to claim 9, further comprising a plurality of said channels randomly disposed within said body.

14. A blood mass transfer device according to claim 9, further comprising a plurality of said channels randomly disposed within said body, wherein each said channel follows a tortuous path.

15. A blood mass transfer device according to claim 9, wherein said body of biphasic, open cell foam comprises polyurethane.

16. A blood mass transfer device according to claim 9, wherein said permeable membrane is gas permeable so that oxygen is transferred across said permeable membrane into the blood and carbon dioxide is transferred across said permeable membrane out of the blood.

17. A blood mass transfer device according to claim 16, wherein said body of biphasic, open cell foam comprises hydrophilic foam.

18. A blood mass transfer device according claim 16, further comprising means disposed within said body for distributing oxygen.

19. A blood mass transfer device according to claim 18, wherein said means for distributing oxygen comprises a plurality of porous fibers.

20. A blood mass transfer device according to claim 9, wherein said permeable membrane is permeable to metabolic waste products so that waste products move out of the blood in said blood pathway.

* * * * *